US010972287B2

(12) United States Patent
Thekadath et al.

(10) Patent No.: US 10,972,287 B2
(45) Date of Patent: Apr. 6, 2021

(54) SYSTEMS AND METHODS FOR CREATING A UNIVERSAL RECORD

(71) Applicant: Visa International Service Association, San Francisco, CA (US)

(72) Inventors: Ajith Thekadath, Foster City, CA (US); Suman Mukherjee, Foster City, CA (US)

(73) Assignee: Visa International Service Association, San Francisco, CA (US)

(*) Notice: Subject to any disclaimer, the term of this patent is extended or adjusted under 35 U.S.C. 154(b) by 160 days.

(21) Appl. No.: 16/338,982

(22) PCT Filed: Nov. 2, 2017

(86) PCT No.: PCT/US2017/059744
§ 371 (c)(1),
(2) Date: Apr. 2, 2019

(87) PCT Pub. No.: WO2018/085558
PCT Pub. Date: May 11, 2018

(65) Prior Publication Data
US 2019/0253258 A1  Aug. 15, 2019

Related U.S. Application Data

(60) Provisional application No. 62/416,957, filed on Nov. 3, 2016.

(51) Int. Cl.
*H04L 29/06* (2006.01)
*H04L 9/32* (2006.01)
(Continued)

(52) U.S. Cl.
CPC ........ *H04L 9/3247* (2013.01); *G06F 16/2228* (2019.01); *G06F 21/602* (2013.01);
(Continued)

(58) Field of Classification Search
CPC ....... H04L 9/3247; H04L 9/0637; H04L 9/30; H04L 9/3239; H04L 2209/38;
(Continued)

(56) References Cited

U.S. PATENT DOCUMENTS 10,547,457 B1 * 1/2020 Duccini ............... H04L 9/3247
2008/0162484 A1 * 7/2008 Yoshida ............. G06F 21/6218
(Continued)

FOREIGN PATENT DOCUMENTS

| WO | 2015175722 | 11/2015 |
|----|-----------|---------|
| WO | 2018067232 | 8/2017 |

OTHER PUBLICATIONS

PCT/US2017/059744, "International Search Report and Written Opinion", dated Jul. 23, 2018, 11 pages.
(Continued)

*Primary Examiner* — Malcolm Cribbs
(74) *Attorney, Agent, or Firm* — Kilpatrick Townsend & Stockton LLP

(57) ABSTRACT

A method for tracking multiple classes of records in a single blockchain is disclosed, the method comprising: by the administrative node computer, receiving, from a first node computer, a request for a class identifier for a certain class, the request including an address identifier associated with the first node computer; generating the class identifier; creating an association between the class identifier and the address identifier; receiving a data element from the first node computer, the data element including the address identifier, the class identifier, and record update information; verifying that the class identifier is associated with the address identifier; verifying that the record update information is permitted according to the class identifier; and creating, a block for a blockchain, the block including the
(Continued)

data element. Class identifiers can used for each record entry to distinguish between classes within the blockchain.

20 Claims, 8 Drawing Sheets

(51) Int. Cl.

| | | |
|---|---|---|
| *G06F 16/22* | (2019.01) | |
| *G06Q 20/02* | (2012.01) | |
| *G06Q 20/06* | (2012.01) | |
| *G16H 10/60* | (2018.01) | |
| *G06F 21/60* | (2013.01) | |
| *H04L 9/06* | (2006.01) | |
| *H04L 9/30* | (2006.01) | |

(52) U.S. Cl.
CPC ............ *G06Q 20/02* (2013.01); *G06Q 20/06* (2013.01); *G16H 10/60* (2018.01); *H04L 9/0637* (2013.01); *H04L 9/30* (2013.01); *H04L 9/3239* (2013.01); *G06Q 2220/00* (2013.01); *H04L 2209/38* (2013.01); *H04L 2209/88* (2013.01)

(58) Field of Classification Search
CPC ..... H04L 2209/88; H04L 63/10; G16H 10/60; G06F 16/2228; G06F 21/602; G06F 21/62; G06F 21/6209; G06F 21/6218; G06F 21/6227; G06Q 20/02; G06Q 20/06; G06Q 2220/00
See application file for complete search history.

(56) References Cited

U.S. PATENT DOCUMENTS

| | | | |
|---|---|---|---|
| 2010/0217710 A1 | 8/2010 | Fujita | |
| 2011/0068168 A1* | 3/2011 | Graves ................... | G06Q 20/02 235/379 |
| 2012/0124640 A1* | 5/2012 | Bender ............... | G06F 21/6218 726/1 |
| 2013/0297329 A1* | 11/2013 | Banthia .................. | G06Q 10/10 705/2 |
| 2015/0143132 A1* | 5/2015 | Haruki ..................... | G06F 21/54 713/189 |
| 2016/0188617 A1* | 6/2016 | Gaikwad ................. | G06F 16/13 707/785 |
| 2016/0253622 A1* | 9/2016 | Sriram ................... | H04L 63/126 713/179 |
| 2016/0261690 A1 | 9/2016 | Ford | |
| 2016/0283920 A1 | 9/2016 | Fisher et al. | |
| 2016/0292672 A1 | 10/2016 | Fay et al. | |
| 2017/0116693 A1* | 4/2017 | Rae ........................ | H04L 9/3236 |
| 2017/0237554 A1 | 8/2017 | Jacobs | |
| 2017/0359374 A1* | 12/2017 | Smith .................. | G06F 21/6245 |
| 2018/0068091 A1* | 3/2018 | Gaidar .................... | G06F 21/16 |
| 2018/0089436 A1* | 3/2018 | Smith ................... | H04L 9/3236 |

OTHER PUBLICATIONS

EP17867259.8 , "Partial Supplementary European Search Report", dated Oct. 8, 2019, 13 pages.

\* cited by examiner

| FIRST NODE COMPUTER STATIC IDENTIFIERS | CLASSES AVAILABLE TO THE FIRST NODE COMPUTER | RESTRICTIONS PER CLASS | ENTRIES REMAINING |
|---|---|---|---|
| ADDRESS ID: XLKJADF85DASDF7D<br><br>ISSUANCE ID: F98FDFFG776658FGS | CLASS ID #1:<br>ISDFDDF99 | 100 ENTRIES / DAY | 52 |
| | CLASS ID #2:<br>JDFJF8DHA8 | 50 ENTRIES / DAY | 14 |
| | CLASS ID #3:<br>B51BUF66KJ | 20 ENTRIES / DAY | 3 |
| | CLASS ID #4:<br>FJHWER67D | 30 ENTRIES / DAY | 26 |
| | CLASS ID #5:<br>YHVR286BN | 60 ENTRIES / DAY | 47 |

FIG. 4

SYSTEMS AND METHODS FOR CREATING A UNIVERSAL RECORD

CROSS REFERENCE TO RELATED APPLICATIONS

This application is a 371 patent application of International Application No. PCT/US2017/059744, filed Nov. 2, 2017, which is a non-provisional application of and claims the benefit of the filing date of U.S. Provisional Application No. 62/416,957, filed on Nov. 3, 2016, which are herein incorporated by reference in their entirety for all purposes.

BACKGROUND

New technologies are improving systems for record keeping. For example, blockchain technology provides self-referencing and cryptographically secure records that are safe from tampering. However, it can be cumbersome to create and implement secure record keeping systems, such as blockchains. As a result, blockchain systems are often not created unless there is the high chance of the data tampering or the record-keeper has abundant disposable resources. Accordingly, many types of records remain insecure.

Embodiments of the invention address these and other problems individually and collectively.

SUMMARY

Embodiments of the invention provide systems and methods for combining multiple blockchain systems into a single blockchain system. For example, separate types of information, such as medical information, academic achievement information, employee data, access rights, financial transactions, and any other suitable information can all be recorded in a single blockchain. As a result, the effort used to create blockchain record systems is reduced, as several disparate systems can be consolidated into one. Additionally, classes of information that might not have previously had their own blockchains can now be easily incorporated into a universal blockchain.

The universal blockchain can distinguish between different types of recorded information by including a class identifier in each entry. This allows different types of information to be recorded together in a blockchain while still maintaining distinct and intelligible ledgers. Class identifiers can also be uniquely assigned to each node, such that a node's permission for contributing information to a specific record class can be verified by the presence of a valid class identifier.

One embodiment of the invention is directed to a method. The method comprises receiving, by an administrative node computer, a request for a class identifier for a certain class from a first node computer. The request includes an address identifier associated with the first node computer. The method further includes generating the class identifier and creating an association between the class identifier and the address identifier. The method also comprises receiving a data element from the first node computer. The data element includes the address identifier, the class identifier, and record update information. The method further includes verifying that the class identifier is associated with the address identifier, verifying that the record update information is permitted according to the class identifier, and then creating a block for a blockchain, the block including the first data element.

Another embodiment of the invention is directed to an administrative node computer configured to perform the above-described method.

Another embodiment of the invention is directed to a method comprising sending, by a first node computer, a request for a class identifier for a certain class to an administrative node computer. The request including an address identifier associated with the first node computer, and the administrative node computer generates the class identifier and creates an association between the class identifier and the address identifier. The method further includes receiving the class identifier from the administrative node computer, generating a data element including the address identifier, the class identifier, and record update information, and sending the data element to the administrative node computer. The administrative node computer verifies that the class identifier is associated with the address identifier. The administrative node computer also verifies that the record update information is permitted according to the class identifier. The administrative node computer then creates a block for a blockchain, the block including the first data element.

Another embodiment of the invention is directed to a first node computer configured to perform the above-described method.

Further details regarding embodiments of the invention can be found in the Detailed Description and the Figures.

BRIEF DESCRIPTION OF THE DRAWINGS

FIG. 4 shows a diagram of data tags of multiple types associated with a single participant, according to an embodiment of the invention.

DETAILED DESCRIPTION

Figure 1:
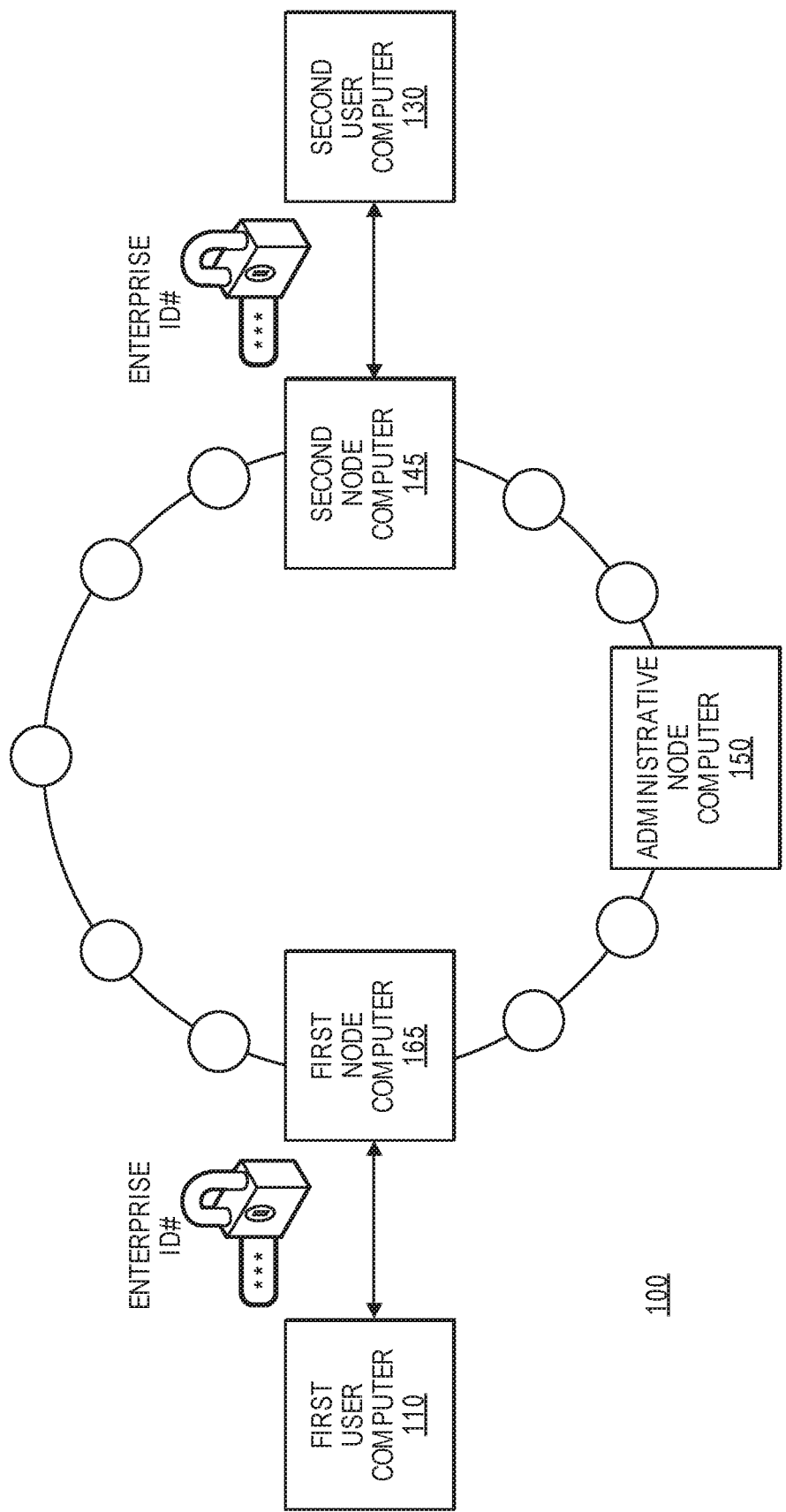
FIG. 1 shows a block diagram of a system according to an embodiment of the invention.

Embodiments of the present invention are directed to utilizing a single blockchain for multiple types of information. For example, medical patient information, biometric data, ownership data, academic credentials, product data, employee achievement information, financial transactions, etc. can all be recorded in a single blockchain. The different sets of information can be distinguished by including a class identifier in each blockchain entry.

For example, embodiments include submitting a data element including new information, and having a class identifier in each data element. The class identifiers serve to distinguish, for example, a transaction using US dollars from a transaction using Japanese yen. Each blockchain in the block can include multiple data elements, each data element being associated with a specific class. A complete ledger for a specific class (e.g., transaction conducted using US dollars) can be compiled by retrieving all data elements associated with that class from the total blockchain.

Additionally, embodiments of the invention provide additional security and trust in the blockchain by incorporating several verified and linked identifiers. For example, a node computer that submits a new data element can include an address identifier, an issuance identifier, and a class identifier in the data element. Each of these identifiers can be uniquely associated with the node and assigned by a trusted, central administrator. If the identifiers are not all used together, a data element may be rejected.

Further, the node's class identifier may only be used for a specific class that the node is authorized for updating. For example, the node may be authorized to issue digital assets based on a US dollar value, but not a British pound value. Before recording a new data element in the blockchain, an administrative node may verify that a class identifier is being used appropriately, that it is accompanied by the correct address identifier and issuance identifier, and that the submitting node has not exceeded a daily spending limit for that class. As a result, if a first node submits a digital asset (e.g., a data element that promises a value transfer), other nodes can be confident that the submitting node has been cleared to issue a digital asset for that specific currency, that the administrator has verified the current use of the class identifier, that a number of other verification steps have taken place, and that therefore a new digital asset is trustworthy and reliable.

Additional features that can be included in embodiments of the invention are described in the International Application US2017/046364, which is incorporated by reference herein in its entirety for all purposes.

Prior to discussing specific embodiments of the invention, some terms may be described in detail.

An "address identifier" may include an identifier for a participant. For example, an address identifier can represent a node or a service provider in a network. In some embodiments, a communication can be directed to a specific node by including the node's address identifier. An address identifier can include a string of characters, such as letters, numbers, etc. For example, an address identifier can be a string of 5, 10, 15, or any other suitable number of characters. In some embodiments, a public key associated with a participant can be used as the participant's address identifier.

An "issuance identifier" may include an identifier indicating that permission is issued. For example, an issuance identifier can serve as evidence that a network participant is authorized to submit new information (e.g., create new data elements for a record). An issuance identifier can include a string of characters, such as letters, numbers, etc. For example, an address identifier can be a string of 5, 10, 15, or any other suitable number of characters.

A "class identifier" may include a value that represents a specific type of record. Class identifiers can be used to identify any suitable class of recordable information. For example, a class identifier can be configured to identify medical information-type records, academic credential-type records, product identifier-type records, employee data-type records, value transfer records of various types (e.g., US dollar payments, British pound payments, Chinese yuan payments, digital right data transfers, property deed transfers, event ticket transfers, game credit transfers, energy credit transfers, mobile phone minute transfers, etc.), or any other suitable type of record. Classes can be divided in any suitable manner. For example, product identifier records can be further divided into a food product class, an office supplies class, an electronic products class, etc.

In some embodiments, a class identifier can also indicate that a specific participant is authorized to create and/or receive data elements for that type of record. For example, a first class identifier can indicate that a first node has permission to submit and/or receive digital assets associated with a US dollar value, and a second class identifier can indicate that a second node has permission to update a public health record. Multiple class identifiers can be assigned to a single node or service provider, each class identifier indicating a certain class of record that the node is authorized to update. A class identifier can include a string of characters, such as letters, numbers, etc. For example, an address identifier can be a string of 5, 10, 15, or any other suitable number of characters.

An "enterprise identifier" may include an identifier for a user. For example, an enterprise identifier can be a globally unique identifier for an end user that submits new record information to a node in a record-keeping network, or for an end user that receives information about new record information (e.g., a value transfer) from a node. In some embodiments, an enterprise identifier can also indicate a specific node with which a user is associated. Additionally, an enterprise identifier can be valid for use with a specific class of record. An enterprise identifier may include alphanumeric characters, special characters, and any other suitable symbol.

A "data element" may refer to digital information. For example, a data element can be information that exists in binary format. In some embodiments, a data element can include information about anything that can be described in a record. For example, a data element can include any suitable type of digital information, such as medical data, biometric data, ownership data, academic credentials, product data, etc. A data element can also be used to describe an update, a change, or a request. For example, a data element can include digital information about a change in a person's medical status, an update about the number of sick days an employee has used, a request to validate or approve of a value transfer, or a promise to transfer a value from one entity to another. One example of a data element is a digital asset.

A "digital asset" may refer to digital content associated with a value. In some cases, the digital asset may also indicate a transfer of the value. For example, a digital asset may include data that indicates a transfer of a currency value (e.g., fiat currency or crypto currency). In other embodiments, the digital asset may correspond to other non-currency values, such as access privileges data (e.g., a number of authorized usages, a time allotment for accessing information, event tickets, login credentials, etc.), ownership data (e.g., digital right data, a property deed, vehicle ownership credentials, etc.), and usage credit data (e.g., game credit, energy credits, mobile phone minutes, etc.)

The term "node" may refer to a connection point. In some embodiments, a node may be a physical electronic device that is capable of creating, receiving, or transmitting data. In other embodiments, a node may be a software module on a computing device, the software module a connection point in a communication network. In some embodiments, a node may be a computing device within a record-keeping network. A node may be able to create a data element, transfer a data element, receive a data element, validate a data element, access a central record, and/or perform any other suitable functions. Different types of nodes may be able to perform different sets of functions within a recording network. In some embodiments, a node may be associated with and/or operated by a financial institution computer (e.g., a bank), a payment processor computer, a third party computer, or any other suitable entity.

A "record" may refer to evidence of a data element. A digital record can be electronic documentation of a data element. A record can include a record identifier and record information. For example, record information can include information a data element (e.g., a digital asset) and/or information about the data element (e.g., a digital signature associated with the digital asset). A record identifier can be a number, title, or other value used for identifying a record. A record identifier can be nondescript, in that it may not provide any meaningful information about the record information in the record. Examples of records include medical records, academic records, transaction records within a ledger of transactions, etc. Another example of a record is a block in a blockchain. An individual block can be an individual record, and a blockchain can be a series of records. A blockchain header is an example of a record identifier, and a blockchain body is an example of record information.

The term "ledger of transactions" may refer to a compilation of data from previous transactions. The ledger of transactions may be a database or other comparable file structure that may be configured to store data from all previous digital asset transfers, including the date and time of the transfer, the transfer amount, and identification information for the participants of the transfer (e.g., the sender and the receiver of the transfer amount). In some embodiments, the ledger of transactions may be in the form of an electronic ledger (e.g., blockchain) in which data already stored in the electronic ledger is unalterable.

As used herein, a "blockchain" may comprise a series of blocks. Each block in the blockchain may include an electronic record of one or more historical transactions, as well as metadata. In some embodiments, blocks in the blockchain can be linked by including a reference to the previous block (e.g., a hash output of a previous block). Each new block in the blockchain may be algorithmically determined based on new transactions and previous blocks in the blockchain. As a result, any tampering of data stored in these previous blocks can be detected.

A "key pair" may include a pair of linked encryption keys. For example, a key pair can include a public key and a corresponding private key. In a key pair, a first key (e.g., a public key) may be used to encrypt a message, while a second key (e.g., a private key) may be used to decrypt the encrypted message. Additionally, a public key may be able to authenticate a digital signature created with the corresponding private key. The public key may be distributed throughout a network in order to allow for authentication of messages signed using the corresponding private key. Public and private keys may be in any suitable format, including those based on RSA or elliptic curve cryptography (ECC). In some embodiments, a key pair may be generated using an asymmetric key pair algorithm. However, a key pair may also be generated using other means, as one of ordinary skill in the art would understand.

The term "digital signature" may refer to an electronic signature for a message. A digital signature may be a numeric value, an alphanumeric value, or any other type of data including a graphical representation. A digital signature may be a unique value generated from a message and a private key using an encrypting algorithm. In some embodiments, a validation algorithm using a public key may be used to validate the signature.

A "server computer" may include a powerful computer or cluster of computers. For example, the server computer can be a large mainframe, a minicomputer cluster, or a group of servers functioning as a unit. In one example, the server computer may be a database server coupled to a Web server. The server computer may be coupled to a database and may include any hardware, software, other logic, or combination of the preceding for servicing the requests from one or more client computers.

FIG. 1 shows a system 100 comprising a number of components. The system 100 comprises a recording network that is administered by an administrative node computer 150. The first node computer 165, the second node computer 145, and any other suitable number of node computers participate in the network. The first user computer 110 operated by a first user (not shown) can submit record update instructions via the first node computer 165, and the second user computer 130 operated by a second user (not shown) can receive record updates via the second node computer 145. All of the computers shown in the system 100 may be in operative communication with each other through any suitable communication channel or communications network. Suitable communications networks may be any one and/or the combination of the following: a direct interconnection; the Internet; a Local Area Network (LAN); a Metropolitan Area Network (MAN); an Operating Missions as Nodes on the Internet (OMNI); a secured custom connection; a Wide Area Network (WAN); a wireless network (e.g., employing protocols such as, but not limited to a Wireless Application Protocol (WAP), I-mode, and/or the like); and/or the like.

Messages between the computers, networks, and devices may be transmitted using a secure communications protocols such as, but not limited to, File Transfer Protocol (FTP); HyperText Transfer Protocol (HTTP); Secure Hypertext Transfer Protocol (HTTPS), Secure Socket Layer (SSL), ISO (e.g., ISO 8583) and/or the like.

The system 100 can be configured to maintain multiple types of records via a single recording network. The administrative node computer 150 can administrate the recordkeeping process by providing a number services. For example, the administrative node computer 150 can build new blocks for a blockchain, the new blocks including updated record information. The administrative node computer 150 can also enroll nodes and end users, as well as regulate the behavior of participating nodes in order to keep the records secure and reliable. The administrative node computer 150 can further verify new data elements and inform participating nodes about new data elements and blocks.

While the administrative node computer 150 can build and maintain the records, the first node computer 165 and the second node computer 145 can submit new information to the administrative node computer 150 for recording. The first node computer 165 and the second node computer 145 can do this by creating and submitting data elements of various classes. The first node computer 165 and the second node computer 145 can create data elements based on information received from the first user computer 110 and/or the second user computer 130.

While FIG. 1 specifically illustrates the first node computer 165 and the second node computer 145, the system 100 can include any suitable number of additional node computers (as represented by the empty circles in FIG. 1). Additionally, the first node computer 165 and second node computer 145 can communicate with other user computers beyond the first user computer 110 and the second user computer 130. Further, the system 100 can include more than one administrative node computer 150 for administering the recording network.

The system 100 may be used to process, approve, and record any suitable type of information. For example, the system 100 can be used to record data elements with new medical patient data, new academic achievements, new value transfers, etc. Further, the system 100 can maintain multiple types of information in a single blockchain record.

Figure 2:
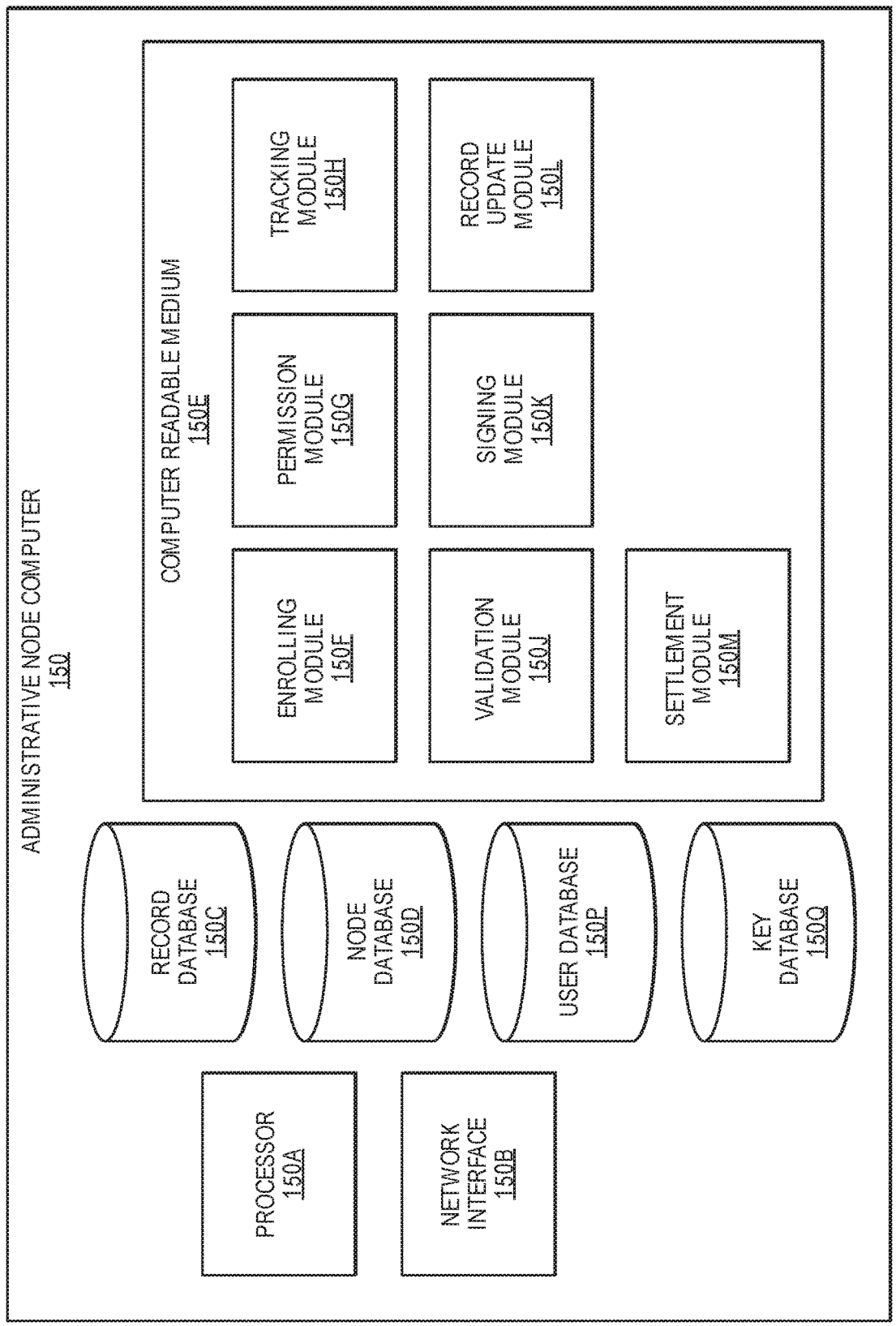
FIG. 2 shows a block diagram of an administrative node computer, according to an embodiment of the invention.

An example of an administrative node computer 150, according to some embodiments of the invention, is shown in FIG. 2. The administrative node computer 150 comprises a processor 150A, a network interface 150B, a record database 150C, a node database 150D, a user database 150P, a key database 150Q, and a computer readable medium 150E.

The record database 150C can store records. For example, data elements received from nodes in the network can be inserted into a record and stored in the record database 150C. In some embodiments, the records can take the form of a blockchain with block records, each block including one or more data elements.

The node database 150D can include information about nodes, such as the first node computer 165 and the second node computer 145. For example, the node database can include identifiers associated with the first node computer 165, such as an address identifier, an issuance identifier, and one or more class identifiers. The node database 150D can also include information about restrictions associated with different nodes. For example, the node database 150D can store a spending limit (e.g., $400,000 a day) associated with a first class identifier (e.g., for US dollars) of the first node computer 165, as well as a spending limit (e.g., ¥700,000 a week) associated with a second class identifier (e.g., for Chinese yuan) of the first node computer 165. The node database 150D can also include information about progress toward the spending limits (e.g., $56,832 remaining for US dollars).

The user database 150P can include information about enrolled end users, such as the first user and the second user, as well as devices associated with the users (e.g., the first user computer 110 and the second user computer 130). This can include enterprise identifiers, as well as information about which node the user is associated. For example, the second user computer's enterprise identifier can be associated with the second node computer's address identifier, as well as a specific class identifier and issuance identifier.

The key database 150Q can store encryption keys. For example, the key database 150Q can include a public key for each node, as well as a private key associated with the administrative node computer 150. In some embodiments the key database 150Q can take the form of a hardware security module (HSM).

The computer readable medium 150E may comprise an enrolling module 150F, permission module 150G, tracking module 150H, validation module 150J, a signing module 150K, a record update module 150L, a settlement module 150M, and any other suitable software module. The computer readable medium 150E may also comprise code, executable by the processor 150A for implementing a method comprising receiving from a first node computer, a request for a class identifier for a certain class, the request including an address identifier associated with the first node computer; generating the class identifier; creating an association between the class identifier and the address identifier; receiving a data element from the first node computer, the data element including the address identifier, the class identifier, and record update information; verifying that the class identifier is associated with the address identifier; verifying that the record update information is permitted according to the class identifier; and creating a block for a blockchain, the block including the first data element.

The enrolling module 150F may comprise code that causes the processor 150A to enroll node computers for joining the recording network. For example, the enrolling module 150F may contain logic that causes the processor 150A to evaluate whether or not an entity can enroll, as well as what level of risk to assign to a new entity. A risk level can be affected by whether the entity is a well-known and reliable organization, whether it has established a settlement account or other settlement processes, whether it is located in a risky country, etc. In addition to assigning a risk level, the administrative node computer 150 can issue activity limits for the node based on the risk profile. Activity limits can include, for example, maximum transaction threshold limits and/or velocity limits, such as a limit on the number of digital assets or total digital asset value that can be submitted within a certain time period (e.g., a day, a week, or a month).

The enrolling module 150F may also include instructions for generating and assigning a unique address identifier for a newly enrolled node. Additionally, there may be instructions for generating and distributing keys to a newly enrolled node. For example, the administrative node computer 150 may generate a key pair for a node. The administrative node computer 150 can store the public key and provide the private key to the node computer.

The enrolling module 150F can further include instructions for enrolling end users. For example, the administrative node computer 150 can receive information about a new user (e.g., a name, address, account number, phone number, a business' corporate profile, etc.) from a node, store the user information, and then assign a unique enterprise identifier to the user. In some embodiments, the enterprise identifier can include a subset of characters that are indicative of the associated node or the node's address identifier.

The permission module 150G may comprise code that causes the processor 150A to assign permissions to nodes. For example, the permission module 150G may contain logic that causes the processor 150A to generate and assign an issuance identifier to a node computer (e.g., based on an analysis of a risk profile). The issuance identifier can serve as proof that a node computer is generally authorized to create and submit and/or receive data elements.

The permission module 150G can also, in conjunction with the processor 150A, generate and assign one or more class identifiers to a node computer. Each class identifier can be associated with a limit. For example, the first node computer 165 can be issued a class identifier indicating that the first node computer 165 can submit data elements for updating medical patient information, but the first node computer 165 may be limited to using this class identifier at most five times a day.

The permission module 150G further include instructions for associating all of the node's identifiers and restrictions. For example, the first node computer's address identifier, issuance identifier, first class identifier, second class identifier, and class restrictions can all be linked and stored in the node database 150D.

The tracking module 150H may comprise code that causes the processor 150A to track and monitor class restrictions. For example, the tracking module 150H may contain logic that causes the processor 150A to sum the total transaction amount (e.g., $597) or number of transactions (e.g., 4 transactions) submitted by the first node computer 165 for a given class (e.g., US dollars) within a given time period (e.g., 1 week). If the first node computer 165 submits a new digital asset that exceeds a specified limit for the class (e.g., $1000 US dollars per week), the tracking module 150H can, in conjunction with the processor 150A, reject the digital asset, issue a warning, and/or place a temporary hold on first node computer's activities.

FIG. 4 shows a visual representation of the information that the administrative node computer 150 generates, stores, and tracks for each node computer. This information can be stored in the node database 150D. While FIG. 4 shows information associated with a single node computer, the administrative node computer 150 can maintain this type of information for each node computer.

As shown in FIG. 4, the administrative node computer 150 recognizes a specific node computer based on a unique address identifier. A unique issuance identifier can accompany the address identifier for each submitted data element. Several class identifiers for different classes of data elements (e.g., US dollar transfers, medical record updates, mobile phone minute transfers, academic achievement record updates, and British pound transfers) can be associated with the address identifier and issuance identifier. Restrictions for each class identifier can be noted, and the usage of each class identifier can be monitored such that the remaining usage can be tracked.

Referring back to FIG. 2, the validation module 150J may comprise code that causes the processor 150A to validate a new data element so that the data element can be entered in the records. For example, the validation module 150J may contain logic that causes the processor 150A to check that the data element includes an address identifier, an issuance identifier, and a class identifier that are all valid and associated with the same node computer. The validation module 150J can also include instructions to check that limits associated with the submitted class identifier have not been exceeded and are not currently being exceeded by the new data element.

The validation module 150J may further contain logic that causes the processor 150A to verify that all entities associated with the data element (e.g., one or more nodes, and one or more users) are registered with the network and have been screened for compliance. The administrative node computer 150 can also evaluate transaction risk, for example by assessing the transaction velocity of one or more parties involved, or by determining whether the submitting node has any warnings issued.

The validation module 150J may further comprise code that causes the processor 150A to verify the authenticity of a digital signature. For example, the validation module 150J may contain logic that causes the processor 150A to use the node computer's public key to verify the authenticity of a digital signature associated with that node computer.

The signing module 150K may comprise code that causes the processor 150A to generate digital signatures. For example, the signing module 150K may contain logic that causes the processor 150A to generate a digital signature for a data element using an administrative node private key. The administrative node computer's digital signature can serve to indicate the authenticity of a data element, and can provide a guarantee that a transfer is valid and trustworthy. In some embodiments, the administrative node computer's digital signature can be considered a cosigning of the digital asset, indicating that the administrative node computer 150 will deliver a promised value to the recipient if the payor does not deliver. Further, the digital signature can activate a smart contract that holds the first node computer 165 liable for the sending amount in the originating currency. For example, a smart contract can automatically initiate a settlement process after a certain amount of time. In some embodiments, the administrative node computer 150 can force settlement between a two accounts at a central bank.

The record update module 150L may comprise code that causes the processor 150A to maintain and update a set of records. For example, the record update module 150L may contain logic that causes the processor 150A to record information about a new data element. In some embodiments, the record update module 150L may include instructions for including a new data element in the next block in a blockchain.

The record update module 150L may further include instructions for, when a new data element is created, informing the parties associated with the data element. For example, when a new digital asset is validated and signed, the administrative node computer 150 may send information about the new digital asset to a receiving node (e.g., the second node computer 145) and/or the user computers.

In some embodiments, the participating node computers may not maintain a separate set of records, and may instead refer to the centrally-maintained records of the administrative node computer 150. For example, the first node computer 165 and the second node computer 145 may each be light nodes. In such a case, the administrative node computer 150 may provide these nodes with real-time access to the central records, or the administrative node computer 150 may provide regular record updates (e.g., updates can be sent every 10 seconds, 1 minute, 5 minutes, etc.). As a result, other nodes may be aware of new data elements immediately or soon after the data elements are recorded.

In some embodiments, participating node computers may not be able to see all of the record information, and they may instead have a filtered or permissioned view of the records. For example, the first node computer 165, the second node computer 145, the first user computer 110, and/or the second user computer 130 may only be able to view data elements with which they are associated (e.g., transactions to which they are a party) when accessing the records at the administrative node computer 150. For example, the second node computer 145 may be able to view all block headers, but may only be able to view block bodies and data elements with which it is associated.

In some embodiments, there may be multiple administrative node computers 150 that each receive and process different data elements, and then update their own records. These different administrative node computers may communicate with one another to share new records and to confirm that their records have the same data elements.

The settlement module 150M may comprise code that causes the processor 150A to settle a promised value between accounts. For example, the settlement module 150M may contain logic that causes the processor 150A to debit the first node's settlement account at a central bank by an amount indicated in a data element, and to credit the second node's settlement account with that same amount (or that amount less assessed fees).

In some embodiments, the settlement module 150M can include instructions for converting from a first currency to a second currency during settlement. This can be accomplished by, for example, separating the settlement transaction into two separate transactions. The first settlement transaction can include debiting the first node's account by a first amount in a first currency (e.g., US dollars), and then crediting a first account of the central bank (e.g., a US dollar account) by the same amount with the same type of currency. The second settlement transaction can include debiting a second account of the central bank (e.g., a Chinese yuan account) by a second amount in a second currency (e.g., Chinese yuan), and then crediting the second node's account by the same amount with the same type of currency (e.g., Chinese yuan).

Referring back to FIG. 1, the first node computer 165 can, as mentioned above, participate in the recording network by creating and submitting new data elements for updating the records on behalf of one or more users.

Figure 3:
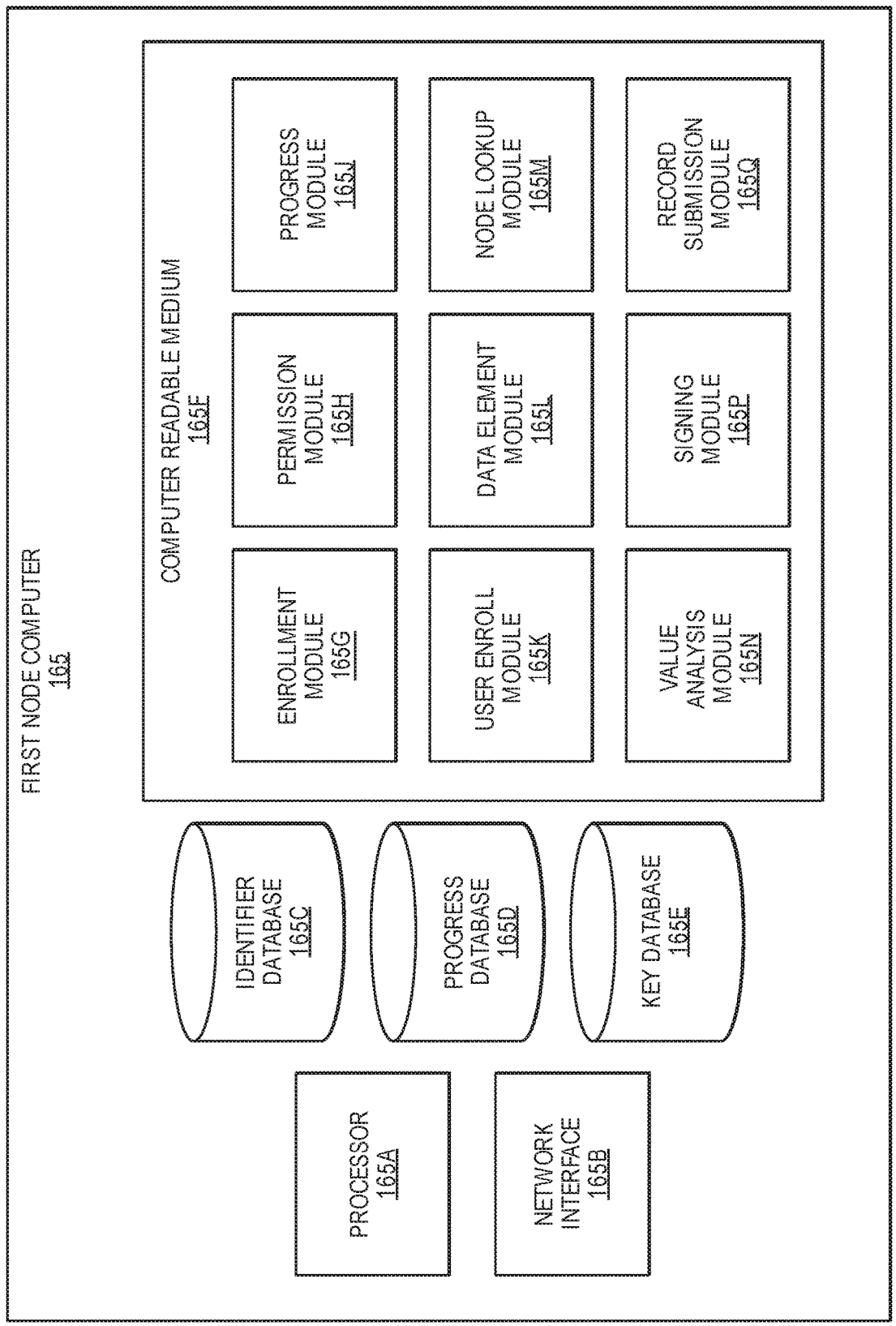
FIG. 3 shows a block diagram of a first node computer, according to an embodiment of the invention.

An example of a first node computer 165, according to some embodiments of the invention, is shown in FIG. 3. The first node computer 165 comprises a processor 165A, a network interface 165B, an identifier database 165C, a progress database 165D, a key database 165E, and a computer readable medium 165F.

The identifier database 165C can store information about the first node computer's identifiers, such as an address identifier, an issuance identifier, and one or more class identifiers. The identifier database 165C may also include information about one or more users, such as an enterprise identifiers, an associated class type, and/or a user account.

The progress database 165D can include information about class restrictions and/or progress toward those restrictions. In some embodiments, the identifier database 165C and the progress database 165D can include the information described above with respect to FIG. 4.

The key database 165E can store encryption keys. For example, the key database 165E can include a private key associated with the first node computer 165, as well as a public key associated with the administrative node computer 150. In some embodiments the key database 165E can take the form of a hardware security module (HSM).

The computer readable medium 165F may comprise an enrollment module 165G, a permission module 165H, a progress module 165J, a user enroll module 165K, a data element module 165L, a node lookup module 165M, a value analysis module 165N, a signing module 165P, a record submission module 165Q, and any other suitable software module. The computer readable medium 165F may also comprise code, executable by the processor 165A for implementing a method comprising sending a request for a class identifier for a certain class to an administrative node computer, the request including an address identifier associated with the first node computer, wherein the administrative node computer generates the class identifier and creates an association between the class identifier and the address identifier; receiving the class identifier from the administrative node computer; generating a data element including the address identifier, the class identifier, and record update information; and sending the data element to the administrative node computer, wherein the administrative node computer verifies that the class identifier is associated with the address identifier, wherein the administrative node computer verifies that the record update information is permitted according to the class identifier; and wherein the administrative node computer creates a block for a blockchain, the block including the first data element.

The enrollment module 165G may comprise code that causes the processor 165A to enroll with the administrative node computer 150 for participation in the recording network. For example, the enrollment module 165G may contain logic that causes the processor 165A to send an enrollment request message including information about the first node, such as an address, a bank identifier, a settlement account, and/or any other suitable information. The enrollment module 165G also include instructions for receiving and storing an address identifier, an administrative node public key, a first node private key, and any other suitable enrollment information from the administrative node computer 150.

The permission module 165H may comprise code that causes the processor 165A to obtain permission for creating and submitting data elements. For example, the permission module 165H may contain logic that causes the processor 165A to send a permission request message to the administrative node computer 150, the message indicating one or more specific record classes. The permission module 165H can also include instructions for receiving and storing permission data, such as an issuance identifier, one or more class identifiers, and information about class restrictions.

The progress module 165J may comprise code that causes the processor 165A to track and monitor progress toward class restrictions. For example, the progress module 165J may contain logic that causes the processor 165A to sum the total number of data elements issued for each class over their specified time periods, the total amount of currency promised for each class over their specified time periods, or otherwise track spending limits (e.g., by updating the progress database 165D). In some embodiments, the first node computer 165 may not proceed with creating a data element requested by the first user computer 110 if the data element would cause a limit to be exceeded.

The user enroll module 165K may comprise code that causes the processor 165A to facilitate enrollment of end users. For example, the user enroll module 165K may contain logic that causes the processor 165A to provide user information (e.g., a name, a residential and/or business address, a date of birth, a phone number, an account number, an account username, an account password, an email address, a government-issued identification number such as a driver's license number, passport number, or social security number, etc.) to the administrative node computer 150. The first node computer 165 can also receive and store an enterprise identifier for the first user computer 110 from the administrative node computer 150, and provide the enterprise identifier to the first user computer 110.

The data element module 165L may comprise code that causes the processor 165A to generate a new data element. For example, the data element module 165L may contain logic that causes the processor 165A to receive a request from the first user computer 110, and to create a data element based on the request.

The node lookup module 165M may comprise code that causes the processor 165A to identify a node based on a user. For example, the node lookup module 165M may contain logic that causes the processor 165A to identify the second node computer based on the second user computer being indicated as a digital asset recipient. For example, the second node's address identifier may be identified based on a subset of characters included in the second user's enterprise identifier, or the address identifier can be associated with the second user's enterprise identifier in a database (e.g., a database accessed at the administrative node computer 150). The node lookup module 165M can also include instructions for adding an identified address identifier to a new data element.

The value analysis module 165N may comprise code that causes the processor 165A to determine a value for a digital asset. For example, the value analysis module 165N may contain logic that causes the processor 165A to determine a first amount in a first currency that will be charged to the first user computer 110 in order to deliver a second amount in a second currency to the second user computer 130. This determination can include looking up a current foreign exchange rate and calculating transfer fees (e.g., both of which can be provided by the administrative node computer 150). The amount debited in the first currency, the amount credited in the second currency, the currency exchange rate, and/or the fees assessed can be included in a new digital asset.

The signing module 165P may comprise code that causes the processor 165A to create a digital signature. For example, the signing module 165P may contain logic that causes the processor 165A to apply a private key and a mathematical algorithm to a data element, such that the digital signature is generated for the data element.

The record submission module 165Q may comprise code that causes the processor 165A to submit a new data element for recording. For example, the record submission module 165Q may contain logic that causes the processor 165A to send a new data element, an associated digital signature, and/or any other suitable information to the administrative node computer 150.

In some embodiments, the first node computer 165 can provide additional services to a user beyond submitting new data elements in the recording network. For example, the first node computer 165 can be a computer associated with a financial institution, a hospital, a government agency, an academic institution, a mobile phone service provider, or any other suitable service provider. Accordingly, in some embodiments, the first node computer 165 can maintain an account on behalf of the user. The account may store identity information, medical records, academic records, financial information, or any other suitable details depending on the type of service provider.

In embodiments where the first node computer 165 is associated with a financial institution, the first node computer 165 may store value on behalf of the user. The first node computer 160 may also be able to provide value (e.g., provide a payment) on behalf of the user. An example of a financial institution is an issuer, which may typically refer to a business entity (e.g., a bank) that issues and maintains an account (e.g., a bank account) for a user.

In some embodiments, the first node computer 165 can be representative of multiple associated computers. For example, the functionality described above for network participation and the functionality associated with banking services can be divided among several cooperative computers.

Referring back to FIG. 1, the second node computer 145 can, as mentioned above, participate in the recording network. In some embodiments, the second node computer 145 can validate the authenticity of a new digital asset (or other data element), and can inform the second user computer 130 about the new information.

The second node computer 145 can validate that a new data element is authentic in one or more manners. For example, the second node computer 145 can verify that the first node computer's digital signature and the administrative node computer's signature are both authentic (e.g., using their respective public keys).

The second node computer 145 can also verify that a valid class identifier is used for the data element. Verifying that there is an authentic class identifier can serve as additional evidence that the administrative node computer 150 has enrolled and authenticated the first node computer 165 for issuing data elements for this specific currency (or other record class), and that therefore the new data element can be trusted.

Further, the second node computer 145 can confirm that an incoming data element is of a class that the second node computer 145 is approved to receive. For example, the second node computer 145 can be associated with a unique address identifier, a unique issuance identifier, and one or more unique class identifiers, and the second node computer 145 can confirm that it has an appropriate class identifier proving it is authorized to receive the data element.

In some embodiments, the second node computer 145 can verify the authenticity of a data element by accessing a central record (e.g., a blockchain record), and confirming that the data element has been added to the records.

The second node computer 145 is primarily described herein as a node that receives a new data element on behalf of the second user computer 130. However, in some embodiments, the second node computer 145 can include some or all of the functionality described above with respect to the first node computer 165. For example, the second node computer 145 can submit new data elements to the recording network on behalf of the second user computer 130 or other associated users. Similarly, in some embodiments, the first node computer 165 can include some or all of the functionality described with respect to the second node computer 145 (e.g., the first node computer 165 can receive and validate data elements on behalf of the first user computer 110).

Similar to the first node computer 165, the second node computer 145 can also be associated with a service provider such as a bank. As a result, the second node computer 145 can host a second user account, and can store and receive a value on behalf of the second user. As an example the second node computer 145 can be associated with an acquirer, which may typically be a business entity (e.g., a commercial bank) that has a business relationship with a particular resource provider or other entity. Some entities can perform both issuer and acquirer functions. Some embodiments may encompass such single entity issuer-acquirers.

In some embodiments, second node computer 145 may have a high-level of trust that a value promised via a digital asset will be delivered, for example because of two valid digital signatures, because of the data element being included in a blockchain record, because of the data element including several associated identifiers (e.g., a class identifier, an issuance identifier, and/or an address identifier), or because of any other suitable evidence. As a result, the second node computer 145 may make a value indicated in a received digital asset immediately usable (e.g., withdrawable) in the second user's account, even if the value has not yet been settled and received.

As explained above, multiple nodes can join the recording network, and each node can send and receive data elements on behalf of multiple users. A user can be an individual, a business, an organization's record-updating administrator, or any other suitable type of user. For example the first user can be an individual, and the second user can be a resource provider (e.g., a merchant) that engages in transactions and can sell goods or services, or provide access to goods or services.

In some embodiments, an end user can be associated with multiple enterprise identifiers. For example, a different enterprise identifier may be assigned to a user for each different currency and bank with which the user is associated. The first user can have multiple accounts at the first node computer 165, each with a different currency. Accordingly, the first user computer 110 can store a different enterprise identifier for each type of currency used with the first node computer 165. The first user may also engage in transactions using another account at a separate bank node, and may have another enterprise identifier associated with this additional bank.

As mentioned above, in some embodiments, the recording system may utilize a blockchain. Each block in the blockchain may include information about one or more data elements. A blockchain ledger may be unalterable without detection. For example, each block may include a data header that includes a hash of the previous block in the blockchain ledger and a root value of all past transactions. Since each block in the blockchain ledger may be generated in a similar manner by including a data header storing information referencing its previous entry and previous transactions, no entry can be modified without affecting all following entries. This ensures that any tampering of information related to transactions, such as an attempt to reassign a digital asset to an inappropriate entity, will not go unnoticed. Together, a block header and a block body that includes the transaction information (e.g., and any other suitable information) can make up a block.

By incorporating class identifiers that indicate what type of information is being recorded, a single blockchain can be used for recording multiple classes of information. For example, a single blockchain include information about payment transactions of various currencies, information about other value transfers, medical information, academic information, employee information, etc.

Figure 5:
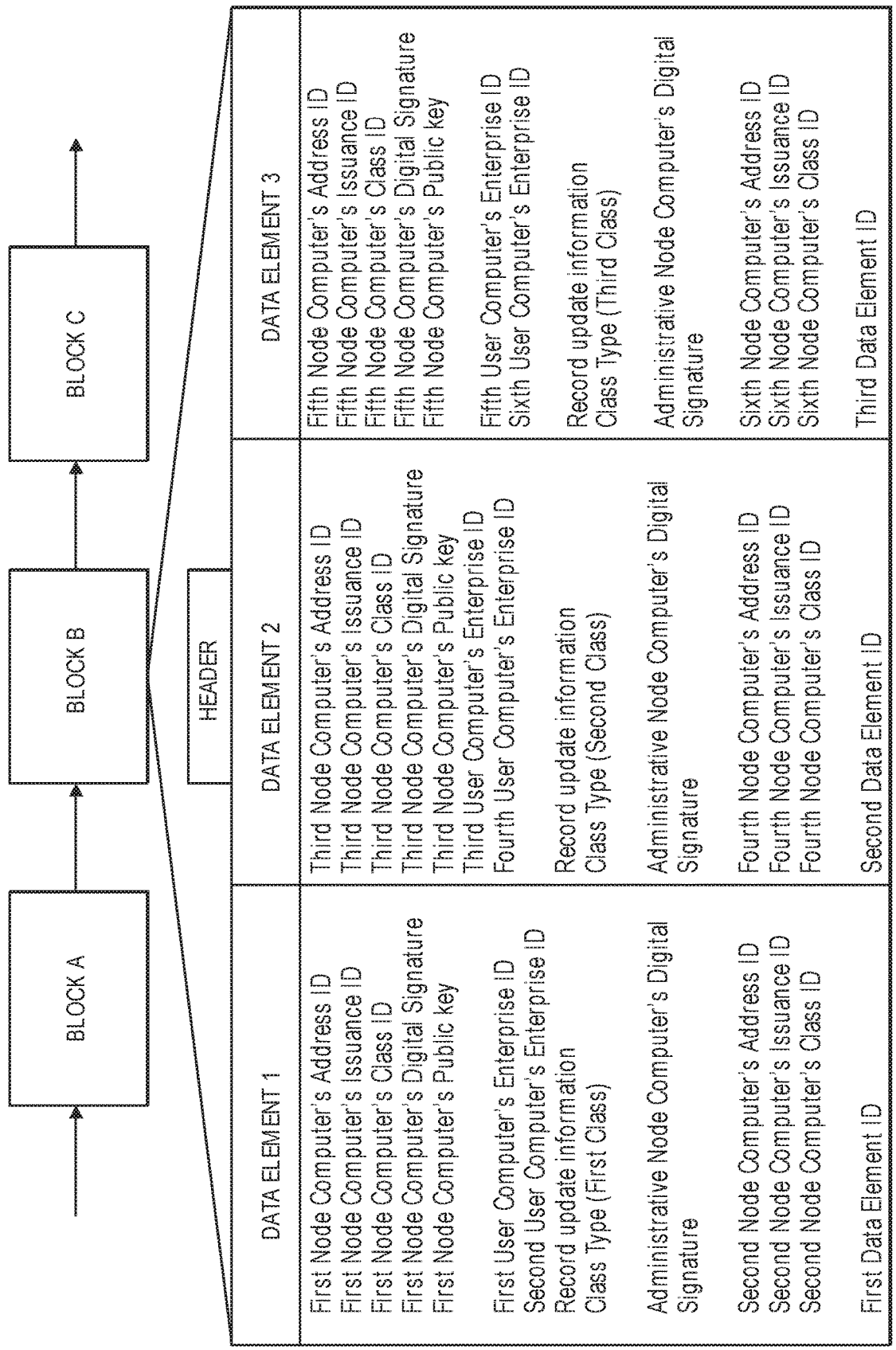
FIG. 5 shows an example of a block in a blockchain, according to an embodiment of the invention.

FIG. 5 shows an example of the information stored in a blockchain block. The example Block B is expanded to show some of the information in Block B. This example block includes three data elements and a hash header. Each data element includes information describing how a ledger (or other data set) is being updated.

For example, the data element 1 can include information about the node that submitted the data element (e.g., the first node computer 165). This can include the first node's address identifier, issuance identifier, class identifier, digital signature, and public key.

Data element 1 can also include information about the involved end users, such as an enterprise identifier associated with the user (e.g., the first user computer 110) that provided the new information to the first node. In embodiments where the data element is a digital asset, the digital asset can include information about a digital asset recipient. The recipient (e.g., the second user computer 130) can be identified by a second enterprise identifier.

Data element 1 further includes the record update information. For example, this can be new medical information, new academic achievement information, new employee information, or information about a new payment transaction (e.g., $50 is being sent from the first user to the second user). In some embodiments, in addition to the class identifier, data element 1 can also include a simple indication of the class type of the data element (e.g., US dollars).

As the administrative node computer 150 can validate and approve of the data element, data element 1 can include the administrative node computer's digital signature. Data element 1 can also include information about the receiving node (e.g., where the data element is used for a value transfer with a recipient). This can include an address identifier, an issuance identifier, and/or a class identifier. Further, each data element can include a unique data element identifier (e.g., a transaction identifier).

Embodiments allow data elements to include any other suitable information, such as an administrative node public key, information about a sending currency type and amount, a receiving currency type and amount, a currency exchange rate, fee information, an invoice number (e.g., for an invoice sent by the second user computer 130 to the first user computer 110), a purchase order number, a timestamp, additional first user information (e.g., an account number, a name, contact information), additional second user information, (e.g., an account number, a name, contact information), etc. When the second user receives a digital asset, the second user computer 130 and second node computer 145 may have sufficient information to execute settlement of the transaction.

As shown in FIG. 5, the different data elements can optionally be associated with different classes. Data element 1 may belong to a first class, data element 2 may belong to a second class, and data element 3 may belong to a third class. As an example, the first class can indicate that data element 1 is a digital asset issued to transfer currency in US dollars, the second class can indicate that data element 2 is a digital asset issued to transfer currency in British pounds, and the third class can indicate that data element 3 is submitted to provide information about a new academic achievement (e.g., a Master's degree is being awarded to a specific person).

Embodiments allow the block to include additional information beyond the data elements, such as a reference to a previous block (e.g., a previous block header), a timestamp, a random number, a hash of record information, etc.

Figure 6A:
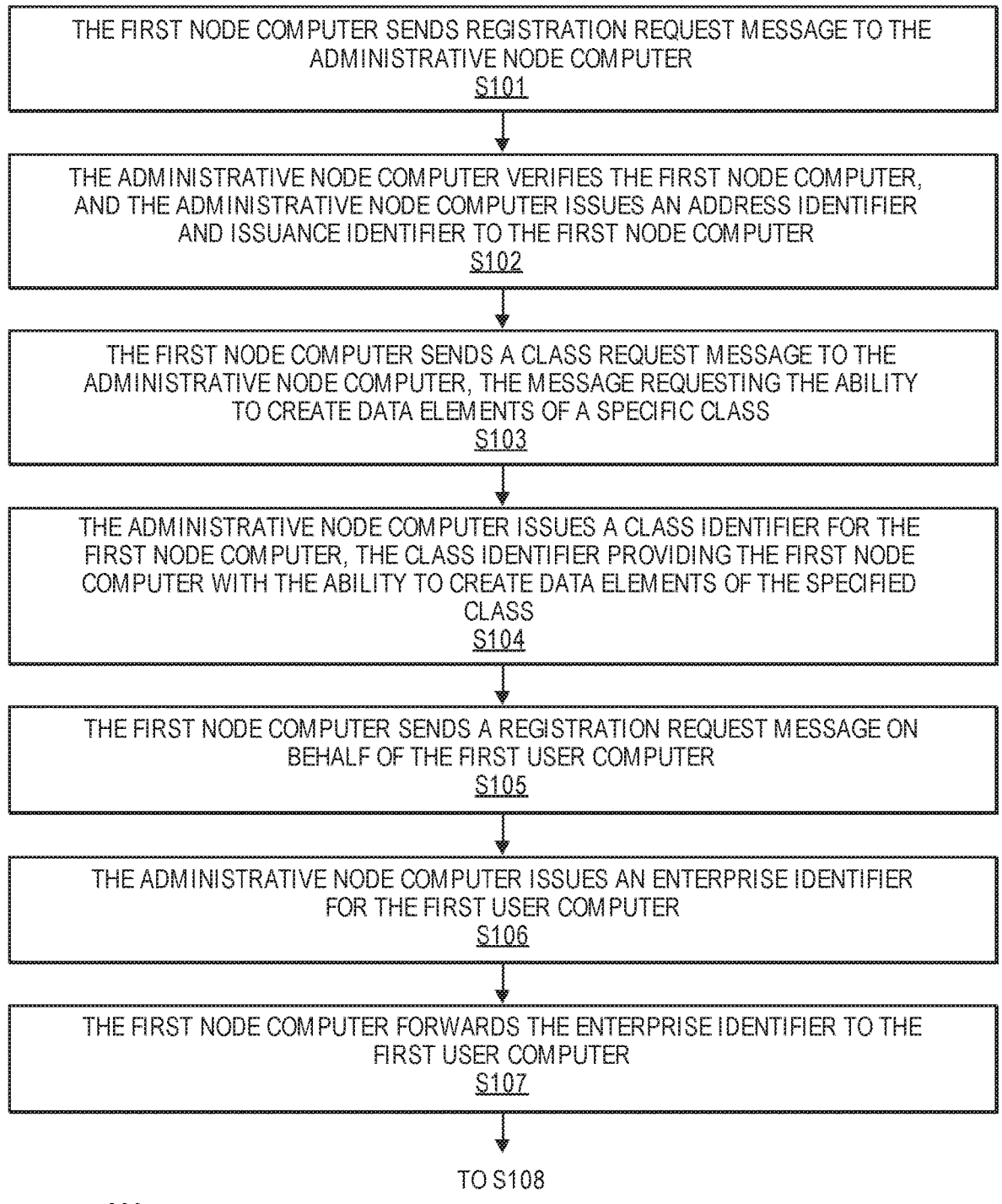
FIGS. 6A-6C shows a flow diagram illustrating a method for creating a blockchain that combines multiple types of information, according to embodiments of the invention.
Figure 6B:
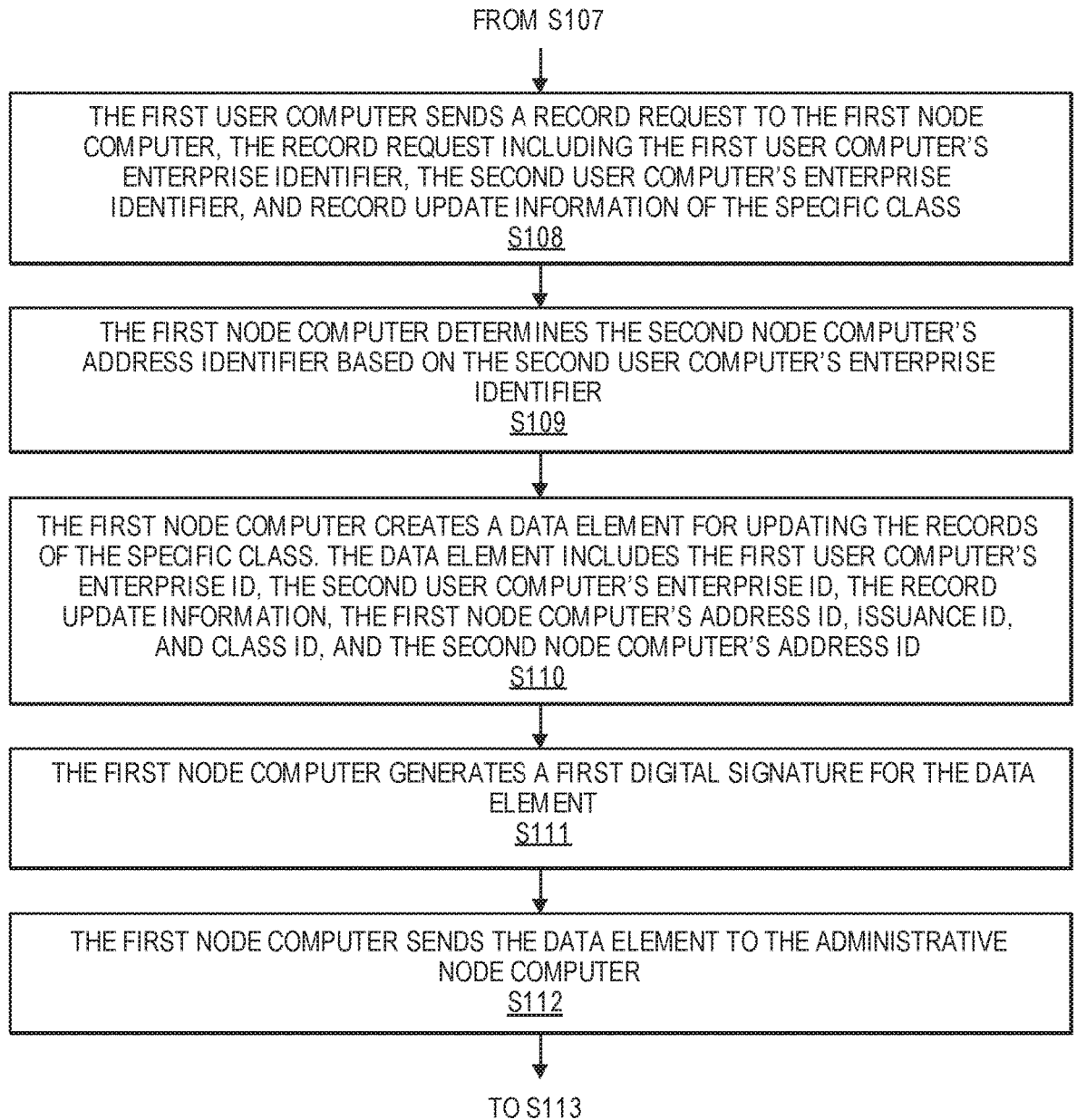
Figure 6C:
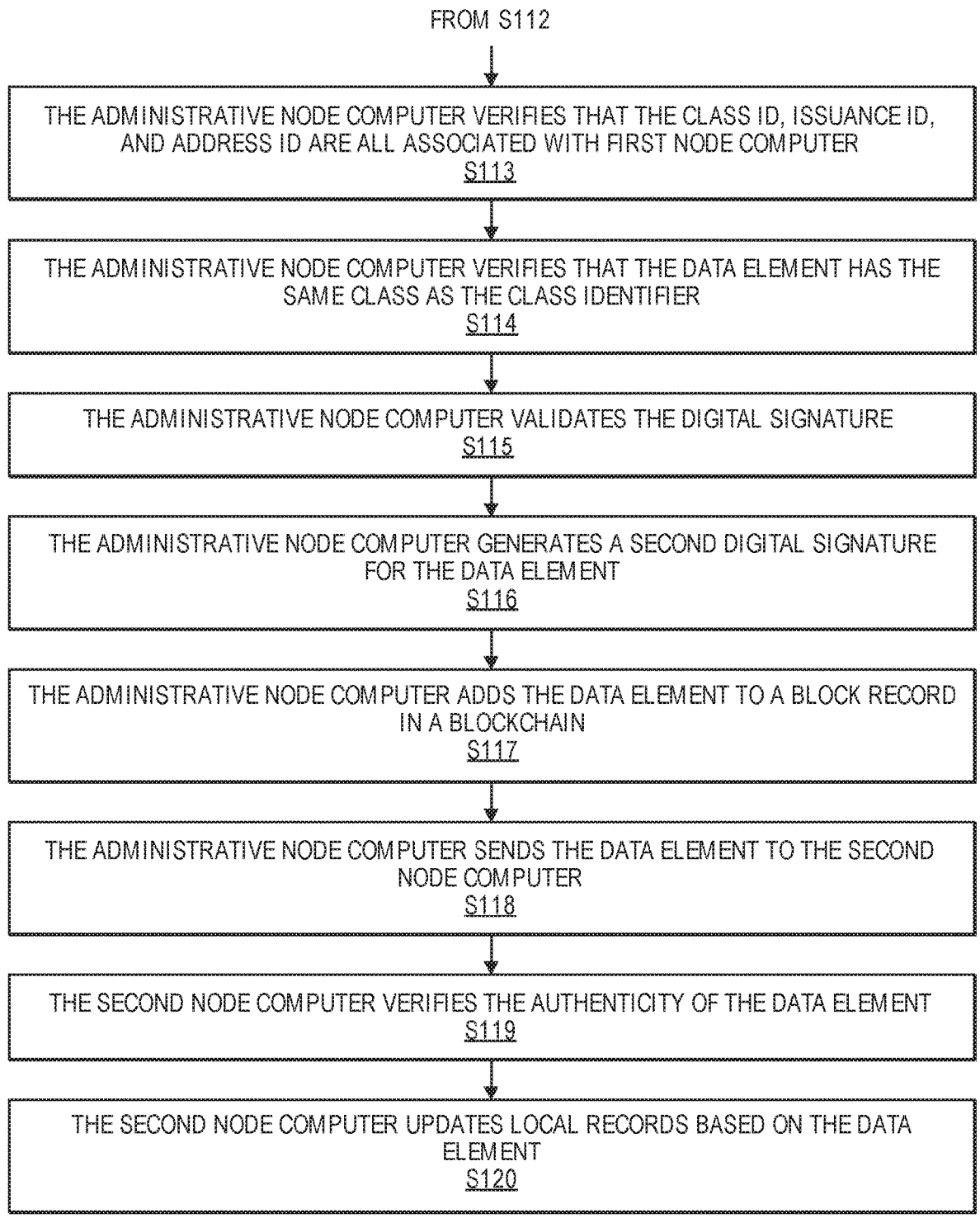

A method 600 according to embodiments of the invention can be described with respect to FIGS. 6A-6C. Some elements in other Figures are also referred to. The steps shown in the method 600 may be performed sequentially or in any suitable order in embodiments of the invention. In some embodiments, one or more of the steps may be optional.

The various messages described below may use any suitable form of communication. In some embodiments, a request or response may be in an electronic message format, such as an e-mail, a short messaging service (SMS) message, a multimedia messaging service (MMS) message, a hypertext transfer protocol (HTTP) request message, a transmission control protocol (TCP) packet, a web form submission. The request or response may be directed to any suitable location, such as an e-mail address, a telephone number, an internet protocol (IP) address, or a uniform resource locator (URL). In some embodiments, a request or response may comprise a mix of different message types, such as both email and SMS messages.

At step S101, the first node computer 165 sends a registration request message to the administrative node computer 150. The registration request message may include information about the first node computer 165 (e.g., an address, an organization name, a bank identifier) and/or any other suitable information. The registration request can also request permission to act as a node and send and/or receive data elements.

At step S102, the administrative node computer 150 enrolls the first node computer 165 for participation in the recording network. The administrative node computer 150 can perform risk analysis to verify whether the first node computer 165 is sufficiently trustworthy to participate in the recording network. The administrative node computer 150 can then issue an address identifier for the first node computer 165. The administrative node computer 150 may also assign an issuance identifier for the first node computer 165 at this point. The issuance identifier may be linked with the address identifier, such that it is only valid when accompanied by the address identifier.

The administrative node computer 150 may store information about the first node computer 165 (e.g., the address identifier and associated issuance identifier), and send a registration response message to the first node computer 165 indicating that the first node computer 165 is successfully enrolled. The response message can include the address identifier and issuance identifier.

At this point, the administrative node computer 150 may also provide any suitable software (e.g., a software development kit) to the first node computer 165 for interacting with the recording network.

At step S103, the first node computer 165 sends a class request message to the administrative node computer 150. The class request message can be used to request the ability to create data elements of a specific class. For example, the first node computer 165 can request permission for submitting digital assets for sending value to a recipient, where the digital asset will be settled using US dollars. The first node computer 165 can request permission for creating any other suitable class of data element, such as data elements with updated medical information, data elements with information about new academic credentials, and digital assets for paying with another asset class (e.g., Japanese yen, bitcoin, mobile phone minutes, etc.).

At this point, or at any other suitable time, the first node computer 165 can also establish a settlement account at a central bank (e.g., a bank administered by the administrative node computer 150), or otherwise establish settlement agreements (e.g., using a correspondent bank that has a central settlement account). The first node computer 165 can indicate, in the class request message, that a settlement account has been established for the desired currency class.

At step S104, the administrative node computer 150 can issue one or more class identifiers for the first node computer 165. The administrative node computer 150 may first determine whether or not to issue a class identifier for the first node computer 165, for example based on a risk profile and whether or not a settlement pathway has been established. The class identifier can provide the first node computer 165 with the ability to create data elements of the specified class. For example, the first node computer 165 can now be able to successfully create and submit a digital asset with a US dollar value if an appropriate class identifier is provided. In some embodiments, the class identifier can both identify a specific class and the specific node, such that only the first node computer 165 can use the class identifier.

Having fully enrolled and obtained an address identifier, an issuance identifier, and a class identifier, the first node computer 165 can facilitate the enrollment of end users. The first user may desire to use the recording network, and may use the first user computer 110 to communicate a request for enrollment to the first node computer 165, as well as a type of currency that the first user would like to use for transactions.

At step S105, the first node computer 165 can send a registration request message to the administrative node computer 150 on behalf of the first user. The first node computer 165 can provide any suitable information about the first user to the administrative node computer 150, such as a name, address, organization information, payment account information (e.g., a balance, and a currency type), a credit score, etc. The first node computer 165 can also identify itself by providing an address identifier, issuance identifier, and/or class identifier with the request message. The class identifier can indicate the currency class with which the user wishes to transact.

At step S106, the administrative node computer 150 can determine whether to enroll the first user (e.g., based on a risk profile). The administrative node computer 150 can also generate and issue an enterprise identifier for the first user computer 110. In some embodiments, the enterprise identifier can only be used for a certain record class and for data elements submitted by the first node computer 165. For example, the administrative node computer 150 can store information specifying that the enterprise identifier is specifically associated with the first node computer's address identifier, issuance identifier, and/or class identifier. Further, in some embodiments, a subset of the enterprise identifier (e.g., 5 characters) can be formatted to indicate an association with the first node computer 165 and/or a record class.

The administrative node computer 150 can transmit the first user computer's new enterprise identifier back to the first node computer 165. Then, at step S107, the first node computer 165 can store the enterprise identifier (e.g., as associated with the first user's account) and forward the enterprise identifier to the first user computer 110. Having enrolled and obtained an enterprise identifier, the first user computer 110 can now initiate the creation and recording of new data elements. For example, if the enterprise identifier is associated with the use of currency, the first user computer 110 can now send payments to another user via the blockchain network.

At step S108, the first user computer 110 sends a record request to the first node computer 165. For example, the first user computer 110 can submit a request for sending a digital asset to the second user computer 130 for a payment transaction. The record request can include the first user computer's enterprise identifier, the recipient's (e.g., the second user computer) enterprise identifier, and record update information for a specific record class. In the payment transaction example, the record update information can comprise an amount and a type of currency to send to the recipient. For example, the first user may wish to send a payment of $1000 in Singapore dollars to the second user, but the first user may wish to make the payment from an account with US dollars.

At step S109, the first node computer 165 determines a node associated with the second user computer 130, such that the digital asset can be addressed to that node. For example, the first node computer 165 can determine the second node computer's address identifier based on the second user computer's enterprise identifier.

At step S110, the first node computer 165 creates a data element for updating the records of the specific class. For example, the first node computer 165 can create a digital asset that promises a payment to the second user computer 130, where the monetary value will be sent using US dollars (e.g., the class is USD). The digital asset can also indicate that the final delivered value (e.g., $1000 SGD), as well as the foreign exchange rate (e.g., 1 USD to 1.3 SGD), the total fees (e.g., $10 USD), and the initial value in US dollars (e.g., $779 USD) that will be withdrawn from the first user's account.

The data element can includes the first user computer's enterprise identifier, the second user computer's enterprise identifier, the record update information, the first node computer's address identifier, the first node computer's issuance identifier, the first node computer's asset identifier, and the second node computer's address identifier. Other information that can be included in the data element is described above with respect to FIG. 5.

In some embodiments, the first node computer 165 can add the second node computer's class identifier to the data element, in addition to the second node computer's address identifier. As a result, the data element can include two class identifiers; a first class identifier of the first node computer 165, and a second class identifier of the second node computer 145. This can be useful for the case where the first node computer 165 is sending the payment using a first currency (e.g., USD) associated with a first class identifier and the second node computer 145 is receiving the payment using a second currency (e.g., SGD) associated with a second class identifier. As a result, the two nodes can transact even if they are not both authorized to transact with a same currency class.

At step S111, the first node computer 165 generates a first digital signature for the data element. For example, the first node computer 165 can generate a one-way hash using some or all of the information in the data element, and then encrypt hash using a private key. The hash value and/or digital signature may be attached to the data element, thereby making the data element data-tampering evident.

At step S112, the first node computer 165 sends the data element and the digital signature to the administrative node computer 150 for validation and entering into a blockchain record.

At step S113, the administrative node computer 150 can verify that the first node computer's class identifier, the first node computer's issuance identifier, and first node computer's address identifier are all valid and associated with one another and the first node computer 165. For example, the administrative node computer 150 can locate the address identifier in a node database and confirm that the issuance identifier and class identifier are associated with it in the node database. If any one of the identifiers does not belong with the other identifiers, the transaction may be rejected by the administrative node computer 150.

At step S114, the administrative node computer 150 can verify that the data element has the same class as the class identifier. For example, if the data element is a digital asset designed to send a value from an account with US dollars, the administrative node computer 150 can verify that the class identifier is also associated with the use of US dollars. If the class identifier does not match the type of record information included in the data element, the administrative node computer 150 may reject the data element.

In some embodiments, as mentioned above, a second class identifier associated with the second node computer 145 can also be included in a digital asset. The administrative node computer 150 can verify that digital asset indicates that the final currency type delivered to the second node computer 145 (e.g., SGD) matches the class type of the second class identifier, or otherwise verify that the second node computer 145 is authorized to receive the payment and currency being sent.

At step S115, the administrative node computer 150 can validate the first node computer's digital signature and/or hash value. For example, the administrative node computer 150 may perform a checksum procedure for the hash value. This can include generating a second hash value based on the digital asset and checking that the second hash value matches the received hash value. The administrative node computer 150 may validate the digital signature using the first node computer's public key. Again, the administrative node computer 150 can reject the data element if the hash or digital signature cannot be validated.

If steps S113-S115 as well as any other suitable verification steps are successfully completed, the administrative node computer 150 can consider the data element valid and proceed with recording the data element. At step S116, the administrative node computer 150 generates a second digital signature for the data element (e.g., using an administrative node computer 150 private key).

At step S117, the administrative node computer 150 can add the data element to a record. For example, the administrative node computer 150 can create a new block for a blockchain, the block including the new data element (e.g., along with one or more other new data elements).

At step S118, the administrative node computer 150 can send a copy of the data element to the second node computer 145. The administrative node computer 150 can also make the blockchain record accessible to the second node computer 145.

At step S119, the second node computer 145 can verify the authenticity of the data element. For example, the second node computer 145 can confirm that the data element has been entered into the blockchain record (e.g., by accessing the blockchain record at the administrative node computer 150). The second node computer 145 can also verify that data element includes two digital signatures; one from the first node computer 165, and one from the administrative node computer 150. The second node computer 145 can also validate the digital signatures (e.g., using the appropriate public keys). Additionally, the second node computer 145 can verify that the data element includes all the appropriate first node identifiers, and that the class identifiers match the indicated currency classes. All of these verifications, in combination, can create a high-level of trust in the authenticity of the data element. Additionally, the administrative node computer 150 can guarantee that the digital asset value will be delivered, even if a problem arises with the first node computer 165.

At step S120, the second node computer 145 can update its local records based on the data element. For example, the second node computer 145 can credit the digital asset's indicated value to the second user's bank account. Because there may be a high-level of trust in the digital asset, the second node computer 145 may credit the second user's account so that the funds can be withdrawn before the digital asset value is settled between the first node and the second node.

At a later time, the digital asset value can be settled between the first node and the second node. For example, batch settlement for multiple digital assets can happen at the end of the day. In some embodiments, settlement can happen in two steps. First, a first value can be debited from the first node's settlement account, and the same first value can be credited to an administrative node settlement account. Second, a second value can be debited from the same administrative node settlement account or a different administrative node settlement account, and the same second value can be credited to the second node's settlement account. The first value and second value can be the same or different (e.g., the second value can be less than the first value by one or more fees). Additionally, the first value and the second value can have different currency types (e.g., the first value can be in USD, and the second value in SGD).

Embodiments of the invention have a number of advantages. For example, in embodiments of the invention, multiple types of information that are normally separate can be recorded together in a single blockchain. Different types of record information can still be distinguished based on class identifiers. Accordingly, multiple blockchain systems can be combined, reducing the burden of creating multiple separate blockchain systems. Additionally, record classes that are typically not in a blockchain (e.g., due to high cost and effort) can now be recorded in a universal blockchain. As a result, recorded information is made more tamperproof, secure, and trustworthy.

Embodiments of the invention also advantageously more increase the trustworthiness of a blockchain ledger. A central, trusted administrator can enroll each node and end user, track participant behavior (e.g., monitor for unusual activity), and make sure that participants do not exceed spending limits. Additionally, each data element can be digitally signed by both the submitting node and the administrative node. The administrative node can also guarantee a transfer value promised by a sending node, and the administrative node can enter a new data element into a secure blockchain. As a result, receiving nodes can be sure that a number of safety checks have been completed, that the data element will not be erased or changed, and that the data element is therefore legitimate and trustworthy.

As additional security measures, each node can be assigned three different identifiers. The address identifier can uniquely identify a node, the issuance identifier can be unique evidence that a node is authorized to create data elements, and a class identifier can be unique evidence that a node is authorized to submit data elements associated with a specific record class. A data element may only be approved if all three of these are used together and within their assigned restrictions. As a result, even if one of these identifiers is compromised and used illegitimately, the illegitimate data element will not succeed because it does not include the other two identifiers (e.g., as well as a valid digital signature, etc.). This can give a receiving node extra confidence that a new data element was legitimately created and submitted by the indicated sending node, and that therefore any promised value will be delivered.

A computer system will now be described that may be used to implement any of the entities or components described herein. Subsystems in the computer system are interconnected via a system bus. Additional subsystems include a printer, a keyboard, a fixed disk, and a monitor which can be coupled to a display adapter. Peripherals and input/output (I/O) devices, which can couple to an I/O controller, can be connected to the computer system by any number of means known in the art, such as a serial port. For example, a serial port or external interface can be used to connect the computer apparatus to a wide area network such as the Internet, a mouse input device, or a scanner. The interconnection via system bus allows the central processor to communicate with each subsystem and to control the execution of instructions from system memory or the fixed disk, as well as the exchange of information between subsystems. The system memory and/or the fixed disk may embody a computer-readable medium.

As described, the inventive service may involve implementing one or more functions, processes, operations or method steps. In some embodiments, the functions, processes, operations or method steps may be implemented as a result of the execution of a set of instructions or software code by a suitably-programmed computing device, microprocessor, data processor, or the like. The set of instructions or software code may be stored in a memory or other form of data storage element which is accessed by the computing device, microprocessor, etc. In other embodiments, the functions, processes, operations or method steps may be implemented by firmware or a dedicated processor, integrated circuit, etc.

Any of the software components or functions described in this application may be implemented as software code to be executed by a processor using any suitable computer language such as, for example, Java, C++ or Perl using, for example, conventional or object-oriented techniques. The software code may be stored as a series of instructions, or commands on a computer-readable medium, such as a random access memory (RAM), a read-only memory (ROM), a magnetic medium such as a hard-drive or a floppy disk, or an optical medium such as a CD-ROM. Any such computer-readable medium may reside on or within a single computational apparatus, and may be present on or within different computational apparatuses within a system or network.

While certain exemplary embodiments have been described in detail and shown in the accompanying drawings, it is to be understood that such embodiments are merely illustrative of and not intended to be restrictive of the broad invention, and that this invention is not to be limited to the specific arrangements and constructions shown and described, since various other modifications may occur to those with ordinary skill in the art.

As used herein, the use of "a", "an" or "the" is intended to mean "at least one", unless specifically indicated to the contrary.

What is claimed is:

1. A method comprising:
   a) receiving, by an administrative node computer, from a first node computer, a request for a class identifier for a certain class, the request including an address identifier associated with the first node computer;
   b) generating, by the administrative node computer, the class identifier;
   c) creating, by the administrative node computer, an association between the class identifier and the address identifier;
   d) receiving, by the administrative node computer, a data element from the first node computer, the data element including the address identifier, the class identifier, and record update information;
   e) verifying, by the administrative node computer, that the class identifier is associated with the address identifier;
   f) verifying, by the administrative node computer, that the record update information is permitted according to the class identifier; and
   g) in response to steps (e) and (f), creating, by the administrative node computer, a block for a blockchain, the block including the data element.

2. The method of claim 1, wherein the data element further includes a first digital signature associated with the first node computer, and further comprising:
   h) verifying, by the administrative node computer, the authenticity of the first digital signature using a public key associated with the first node computer, wherein step (g) is performed further in response to step (h); and
   i) generating, by the administrative node computer, a second digital signature for the data element using a private key.

3. The method of claim 1, wherein the data element further includes an enterprise identifier associated with a user, and further comprising:
   h) verifying, by the administrative node computer, that the enterprise identifier is also associated with the class identifier, wherein step (g) is performed further in response to step (h).

4. The method of claim 1, further comprising:
   h) identifying, by the administrative node computer, a limit associated with the class identifier; and i) verifying, by the administrative node computer, that the data element does not cause the limit to be exceeded, wherein step (g) is performed further in response to steps (h) and (i).

5. The method of claim 1, wherein the class identifier is associated with medical information, and wherein the record update information is permitted if the record update information includes new medical information.

6. An administrative node computer comprising:
   a processor; and
   a computer readable medium, the computer readable medium comprising code, executable by the processor, for implementing a method comprising:
   a) receiving from a first node computer, a request for a class identifier for a certain class, the request including an address identifier associated with the first node computer;
   b) generating the class identifier;
   c) creating an association between the class identifier and the address identifier;
   d) receiving a data element from the first node computer, the data element including the address identifier, the class identifier, and record update information;
   e) verifying that the class identifier is associated with the address identifier;
   f) verifying that the record update information is permitted according to the class identifier; and
   g) in response to steps (e) and (f), creating a block for a blockchain, the block including the data element.

7. The administrative node computer of claim 6, wherein the data element further includes a first digital signature associated with the first node computer, and further comprising:
   h) verifying the authenticity of the first digital signature using a public key associated with the first node computer, wherein step (g) is performed further in response to step (h); and
   i) generating a second digital signature for the data element using a private key.

8. The administrative node computer of claim 6, wherein the data element further includes an enterprise identifier associated with a user, and further comprising:
   h) verifying that the enterprise identifier is also associated with the class identifier, wherein step (g) is performed further in response to step (h).

9. The administrative node computer of claim 6, further comprising:
   h) identifying a limit associated with the class identifier; and
   i) verifying that the data element does not cause the limit to be exceeded, wherein step (g) is performed further in response to steps (h) and (i).

10. The administrative node computer of claim 6, wherein the class identifier is associated with medical information, and wherein the record update information is permitted if the record update information includes new medical information.

11. A method comprising:
    sending, by a first node computer, to an administrative node computer, a request for a class identifier for a certain class, the request including an address identifier associated with the first node computer, wherein the administrative node computer generates the class identifier and creates an association between the class identifier and the address identifier;
    receiving, by the first node computer, the class identifier from the administrative node computer;
    generating, by the first node computer, a data element including the address identifier, the class identifier, and record update information; and
    sending, by first node computer, the data element to the administrative node computer, wherein the administrative node computer verifies that the class identifier is associated with the address identifier, wherein the administrative node computer verifies that the record update information is permitted according to the class identifier; and wherein the administrative node computer creates a block for a blockchain, the block including the data element.

12. The method of claim 11, further comprising:
    generating, by the first node computer, a first digital signature for the data element using a private key associated with the first node computer, wherein the administrative node computer verifies the authenticity of the first digital signature using a public key associated with the first node computer, and wherein the administrative node computer generates a second digital signature for the data element using a private key associated with the administrative node computer.

13. The method of claim 11, further comprising:
    receiving, by the first node computer, from a user, a request to generate the data element, the request including an enterprise identifier associated with the user, wherein the data element further includes the enterprise identifier, and wherein the administrative node computer verifies that the enterprise identifier is also associated with the class identifier.

14. The method of claim 11, wherein the administrative node computer identifies a limit associated with the class identifier, and wherein the administrative node computer verifies that the data element does not cause the limit to be exceeded.

15. The method of claim 11, wherein the class identifier is associated with medical information, and wherein the administrative node computer permits the record update information if the record update information includes new medical information.

16. A first node computer comprising:
    a processor; and
    a computer readable medium, the computer readable medium comprising code, executable by the processor, for implementing a method comprising:
    sending a request for a class identifier for a certain class to an administrative node computer, the request including an address identifier associated with the first node computer, wherein the administrative node computer generates the class identifier and creates an association between the class identifier and the address identifier;
    receiving the class identifier from the administrative node computer;
    generating a data element including the address identifier, the class identifier, and record update information; and
    sending the data element to the administrative node computer, wherein the administrative node computer verifies that the class identifier is associated with the address identifier, wherein the administrative node computer verifies that the record update information is permitted according to the class identifier; and wherein the administrative node computer creates a block for a blockchain, the block including the data element.

17. The first node computer of claim 16, further comprising:
generating a first digital signature for the data element using a private key associated with the first node computer, wherein the administrative node computer verifies the authenticity of the first digital signature using a public key associated with the first node computer, and wherein the administrative node computer generates a second digital signature for the data element using a private key associated with the administrative node computer.

18. The first node computer of claim 16, further comprising:
receiving, from a user, a request to generate the data element, the request including an enterprise identifier associated with the user, wherein the data element further includes the enterprise identifier, and wherein the administrative node computer verifies that the enterprise identifier is also associated with the class identifier.

19. The first node computer of claim 16, wherein the administrative node computer identifies a limit associated with the class identifier, and wherein the administrative node computer verifies that the data element does not cause the limit to be exceeded.

20. The first node computer of claim 16, wherein the class identifier is associated with medical information, and wherein the administrative node computer permits the record update information if the record update information includes new medical information.

* * * * *